United States Patent
Tomlinson et al.

(10) Patent No.: US 10,335,357 B2
(45) Date of Patent: Jul. 2, 2019

(54) SKIN CARE COMPOSITION

(71) Applicant: THE BOOTS COMPANY PLC, Nottingham (GB)

(72) Inventors: Paul James Tomlinson, Nottingham (GB); Mark Johnson, Nottingham (GB); Michael David Bell, Nottingham (GB)

(73) Assignee: THE BOOTS COMPANY PLC, Nottingham (GB)

( * ) Notice: Subject to any disclaimer, the term of this patent is extended or adjusted under 35 U.S.C. 154(b) by 0 days.

(21) Appl. No.: 15/312,086

(22) PCT Filed: May 15, 2014

(86) PCT No.: PCT/GB2014/051496
§ 371 (c)(1),
(2) Date: Nov. 17, 2016

(87) PCT Pub. No.: WO2015/170064
PCT Pub. Date: Nov. 12, 2015

(65) Prior Publication Data
US 2017/0112744 A1  Apr. 27, 2017

(30) Foreign Application Priority Data

May 7, 2014 (GB) .................................. 1408079.0

(51) Int. Cl.
| | | |
|---|---|---|
| A61K 8/64 | (2006.01) | |
| A61K 8/06 | (2006.01) | |
| A61Q 19/00 | (2006.01) | |
| A61K 8/73 | (2006.01) | |
| A61Q 19/08 | (2006.01) | |

(52) U.S. Cl.
CPC .............. *A61K 8/64* (2013.01); *A61K 8/064* (2013.01); *A61K 8/735* (2013.01); *A61Q 19/00* (2013.01); *A61Q 19/005* (2013.01); *A61Q 19/008* (2013.01); *A61Q 19/08* (2013.01); *A61K 2800/70* (2013.01); *A61K 2800/782* (2013.01)

(58) Field of Classification Search
CPC .... A61K 2800/782; A61K 8/064; A61K 8/64; A61K 8/735; A61Q 19/00; A61Q 19/08
See application file for complete search history.

(56) References Cited

U.S. PATENT DOCUMENTS

| | | |
|---|---|---|
| 4,970,252 A | 11/1990 | Sakuta et al. |
| 5,412,004 A | 5/1995 | Tachibana et al. |
| 5,654,362 A | 8/1997 | Schulz, Jr. et al. |
| 5,723,482 A | 3/1998 | Degwert et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 6,852,699 B1 * | 2/2005 | Schonrock ............... A61K 8/64 514/20.1 |
| 2004/0132667 A1 | 7/2004 | Lintner |
| 2006/0029563 A1 * | 2/2006 | Thorel ..................... A61K 8/60 424/70.14 |
| 2010/0215726 A1 | 8/2010 | Roth |
| 2011/0123467 A1 * | 5/2011 | Roth ......................... A61K 8/64 424/59 |
| 2016/0008291 A1 * | 1/2016 | Ischakov .................. B82Y 5/00 424/9.6 |

FOREIGN PATENT DOCUMENTS

| | | |
|---|---|---|
| DE | 4307983 A1 | 9/1994 |
| DE | 202004006865 U1 | 12/2004 |
| EP | 1671673 A1 | 6/2006 |
| JP | 2007-515381 A | 6/2007 |
| JP | 2011-516585 A | 5/2011 |

(Continued)

OTHER PUBLICATIONS

Dow Corning, "HydroBurst Quick Break After Sun", Retrieved from the Internet: <https://www.dowcorning.com/content/publishedlit/FORMUL_01685_after-sun-lotion-formulation.pdf> (2012).
International Application No. PCT/GB2014/051496, International Preliminary Report on Patentability, dated Sep. 30, 2016.
International Application No. PCT/GB2014/051496, International Search Report and Written Opinion, dated Apr. 7, 2015.
Russell-Jones et al., Water-in-oil microemulsions for effective transdermal delivery of proteins, Expert Opin Drug Deliv., 8(4):537-46 (2011).
Search Report for corresponding Great Britain Application No. GB1408079.0 dated Feb. 12, 2015.

*Primary Examiner* — Marcela M Cordero Garcia
(74) *Attorney, Agent, or Firm* — Marshall, Gerstein & Borun LLP

(57) ABSTRACT

A water-in-oil emulsion comprising less than 60% water, and wherein said emulsion comprises an oil phase and a water phase, and wherein the water phase comprises a dipeptide selected from the group consisting of acetyl dipeptide (1) cetyl ester, acetyl dipeptide (3) aminohexanoate, azelaoyl bisdipeptide (10), coumaroyl dipeptide (3), dicetyl dipeptide (9), dipeptide diamino butyroyl benzylamide diacetate, dipeptide (1), dipeptide (10), dipeptide (11), dipeptide (12), dipeptide (15), dipeptide (16), dipeptide (17), dipeptide (18), dipeptide (19), dipeptide (2), dipeptide (20), dipeptide (3), dipeptide (4), dipeptide (5), dipeptide (6), dipeptide (7), dipeptide (8), dipeptide (8) HCL, dipeptide (9), hexanoyl dipeptide (3) norleucine acetate, methyl undecylenoyl dipeptide (16), nicotinoyl dipeptide (22), nicotinoyl dipeptide (23), nicotinoyl dipeptide (24), nicotinoyl dipeptide (26), oleoyl dipeptide (15), palmitoyl dipeptide (10), palmitoyl dipeptide (13), palmitoyl dipeptidel (7), palmitoyl dipeptide (5) diaminobutyroyl hydroxythreonine, palmitoyl dipeptide (5) diaminohydroxybutyrate, palmitoyl dipeptide (7) and mixtures thereof.

16 Claims, 1 Drawing Sheet
Specification includes a Sequence Listing.

(56) References Cited

FOREIGN PATENT DOCUMENTS

| | | |
|---|---|---|
| WO | WO-2005/048968 A1 | 6/2005 |
| WO | WO-2005/049054 A1 | 6/2005 |
| WO | WO-2006/069608 A1 | 7/2006 |
| WO | WO-2007/064687 A1 | 6/2007 |
| WO | WO-2008/130752 A2 | 10/2008 |
| WO | WO-2009/127058 A1 | 10/2009 |
| WO | WO-2010/085532 A2 | 7/2010 |
| WO | WO-2010/136965 A2 | 12/2010 |
| WO | WO-2011/017274 A2 | 2/2011 |
| WO | WO-2012/125183 A1 | 9/2012 |
| WO | WO-2012/143364 A2 | 10/2012 |
| WO | WO-2012/154949 A2 | 11/2012 |
| WO | WO-2013/142249 A1 | 9/2013 |

* cited by examiner

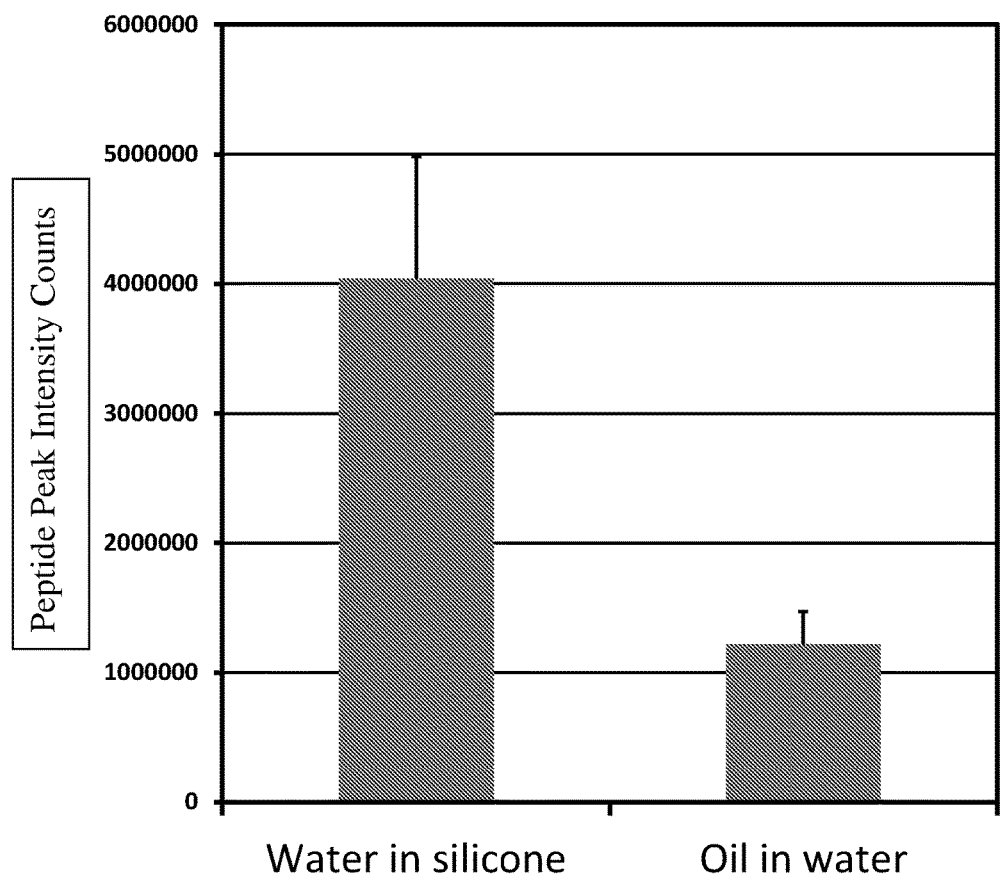

SKIN CARE COMPOSITION

CROSS-REFERENCE TO RELATED APPLICATIONS

This application is the U.S. national phase of PCT/GB2014/051496, filed May 15, 2014, which claims the benefit of United Kingdom patent application no. 1408079.0, filed May 7, 2014, the entire respective disclosures of which are incorporated herein by reference.

INCORPORATION BY REFERENCE OF MATERIAL SUBMITTED ELECTRONICALLY

This application incorporates by reference in its entirety a computer-readable nucleotide/amino acid sequence listing identified as one 4,265 byte ASCII (text) file named "51444_Seqlisting.txt," created Nov. 17, 2016.

TECHNICAL FIELD

The present invention relates to the area of cosmetic beauty emulsion compositions and methods of using said compositions for cosmetic treatment of the skin.

BACKGROUND TO THE INVENTION

Beauty regimes and cosmetic treatment of the skin, especially the face and neck are becoming more common and more desirable. Such products are often directed primarily to improving the health and/or physical appearance of the skin. Amongst these skin care products, many are directed to delaying, minimizing or even eliminating skin wrinkling and other histological changes typically associated with the aging of skin or environmental damage to human skin, such as photodamage. A large number of skin care actives are known in the art and used to improve the health and/or physical appearance of the skin. For example, salicylic acid and benzoyl peroxide are used in skin care compositions to treat acne. Retinoids, are another example of skin care agents, and are used in skin care compositions to reduce signs of aging. Although formulating skin care compositions with such actives provide skin care benefits, there are also challenges in formulating such compositions. Skin care products should be provided in a form suitable for application to the skin, hence semi-viscous creams are preferable over lotions and highly viscous creams. The Applicants have also discovered that the feel of the product on the skin is also highly significant in the perception of efficacy and product experience.

There is therefore a continuing need to formulate skin care compositions which improve the health and/or physical appearance of the skin, which are for example, aesthetically pleasing, stable, and effective in treating the appearance of wrinkles, fine lines and skin tone.

Many preferred components of beauty composition are water soluble and thus, skin care compositions are water based in order to solubilise and/or stabilise said ingredients. However, the Applicants have found that whilst this might be an effective means by which to formulate the composition, the efficacy is reduced since the actives are essentially diluted by the presence of high levels of water. Moreover, said actives may also be easily washed off the skin before they have sufficient time to act. Oily components can provide a functional and/or aesthetic benefit to the skin, or improve the feel of the product on the skin or the delivery of the product to the skin. However, such actives are not soluble in a water based system and if prepared in an oil based system can be perceived as being unappealing, and oily.

The Applicants have surprisingly found that the peptides, particularly the dipeptides of the present invention, and preferably in combination with other peptides, provide exceptional benefits to skin and are most efficacious when delivered in an undiluted environment.

SUMMARY OF THE INVENTION

According to the present invention there is provided a water-in-oil emulsion comprising less than 60% water, and wherein said emulsion comprises an oil phase and a water phase, and wherein the water phase comprises a dipeptide selected from the group consisting of acetyl dipeptide 1 cetyl ester, acetyl dipeptide 3 aminohexanoate, azelaoyl bisdipeptide 10, coumaroyl dipeptide 3, dicetyl dipeptide 9, dipeptide diamino butyroyl benzylamide diacetate, dipeptide 1, dipeptide 10, dipeptide 11, dipeptide 12, dipeptide 15, dipeptide 16, dipeptide 17, dipeptide 18, dipeptide 19, dipeptide 2, dipeptide 20, dipeptide 3, dipeptide 4, dipeptide 5, dipeptide 6, dipeptide 7, dipeptide 8, dipeptide 8 HCL, dipeptide 9, hexanoyl dipeptide 3 norleucine acetate, methyl undecylenoyl dipeptide 16, nicotinoyl dipeptide 22, nicotinoyl dipeptide 23, nicotinoyl dipeptide 24, nicotinoyl dipeptide 26, oleoyl dipeptide 15, palmitoyl dipeptide 10, palmitoyl dipeptide 13, palmitoyl dipeptide17, palmitoyl dipeptide 5 diaminobutyroyl hydroxythreonine, palmitoyl dipeptide 5 diaminohydroxybutyrate, palmitoyl dipeptide 7 and mixtures thereof.

According to a preferred aspect of the present invention the dipeptide is a dipeptide having amino acid sequence selected from the group consisting of Tyr-Arg, Tyr-Val, Ala-Glu, Val-Trp, Asn-Phe, Asp-Phe and mixtures thereof.

The present application also relates to the use of the skin care emulsion of the present invention, in the manufacture of a medicament for regulating the condition of mammalian skin by topical application to the skin of a mammal in need of treatment.

FIGURES

FIG. 1 represents the level of dipeptide permeation into the skin from water in oil and oil in water compositions.

DETAILED DESCRIPTION OF THE INVENTION

The Applicants have importantly found that the dipeptide of the present invention provides superior benefits when delivered in a less diluted environment, as a component of water-in-oil emulsion. The term emulsion is understood to mean a mixture of two or more, normally immiscible liquids. Emulsions can be of different types, oil-in-water, where oil is in the dispersed phase, and water is the dispersion medium, or water-in-oil, where the reverse is true. The present invention is concerned with water-in-oil emulsions, where water is the dispersed phase and oil is the dispersion medium.

Although not wishing to be bound by theory, it is believed that by being a component of the minor water phase, dipeptide is more concentrated. Moreover, when applied to the skin, the water phase of the emulsion will preferentially align with the skin of the user. Since said water phase is more concentrated, a greater proportion of the actives have access to the skin and thus a greater percentage of the actives can be absorbed into the skin before the product is washed off, rubbed off or otherwise removed from the surface of the skin.

Furthermore, the oil phase of the emulsion also provides a number of benefits, including providing an improvement in skin wettability, improved spreadability and thus delivery of product across the skin surface, and providing improved skin feel aesthetics. Moreover, the oil phase acts as a partial occlusive which potentiate the penetration of actives into the skin. Moreover, because the oil phase of the emulsion, when applied to the skin, will sit atop the water phase, it effectively locks the actives in the water phase close to the surface of the skin for a longer period of time. A further benefit of the water-in-oil emulsion is that the oil phase provides a moisturisation benefit and a reduction in transepidermal water loss.

Water-in-Oil Emulsion

The present invention relates to a skin care composition in the form of a water-in-oil emulsion. Water is present at a level of less than 60%, more preferably less than 50%, more preferably less than 45% by weight of the emulsion. Water is preferably present in said emulsion at a level of greater than 10%, more preferably greater than 15%, most preferably greater than 20%. Most preferably water is present in a range of from 35% to 45% of the emulsion composition.

The oil phase of the emulsion can be provided by any suitable oily component. Suitable oils for the oil phase may comprise for example: a) hydrocarbon oils, such as paraffin or mineral oils; b) waxes, such as beeswax or paraffin wax; c) natural oils, such as sunflower oil, apricot kernel oil, shea butter or jojoba oil; d) silicone oils, such as dimethicone, silicone elastomer, cyclomethicone or cetylidimethicone; e) fatty acid esters and ethers, such as isopropyl palmitate or isopropyl myristate and polypropylene glycol-15 stearyl ether; f) fatty alcohols, such as cetyl alcohol or stearyl alcohol; or g) mixtures thereof, for example, the blend of waxes available commercially under the trade name Cutina (BASF). Preferably, the emulsion comprises 0.1% to 55%, more preferably from 15% to 50%, most preferably from 30% to 45% by weight of the emulsion, of oil phase. Preferably the oil phase of the emulsion comprises oil at a level between 50% and 99.9% by weight of the oil phase. More preferably the oil phase comprises oil at a level of from 60% to 99.9%, more preferably from 70% to 99.9%, and even more preferably from 80% to 99.9% by weight of the oil phase.

Preferably the oil phase of the water-in-oil emulsion comprises a silicone oil. Where present, the silicone-containing oil phase preferably comprises an organo polysiloxane oil. The organopolysiloxane oil for use in the composition may be volatile, non-volatile, or a mixture of volatile and non-volatile silicones. The term "nonvolatile" as used in this context refers to those silicones that are liquid or gel under ambient conditions and have a flash point (under one atmospheric of pressure) of greater than 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes can be represented by the general chemical formula

wherein R is an alkyl group having from 1 to 30 carbon atoms (preferably R is methyl or ethyl, more preferably methyl; also mixed alkyl groups can be used in the same molecule), and x is an integer from 0 to 10,000, chosen to achieve the desired molecular weight which can range to over 10,000,000. Commercially available polyalkylsiloxanes include the polydimethylsiloxanes, which are also known as dimethicones, examples of which include those sold by ShinEtsu, Momentive, Wacker and the Dow Corning 200 series sold by Dow Corning Corporation. Specific examples of suitable polydimethylsiloxanes include Dow Corning 2, 20, 100, 200, 225, 300 and mixtures thereof. Suitable dimethicones include those represented by the chemical formula

wherein R is straight or branched chain alkyl having from 2 to 30 carbon atoms and x and y are each integers of 1 or greater selected to achieve the desired molecular weight which can range to over 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2-O]n$ wherein R is an alkyl group, preferably R is methyl or ethyl, more preferably methyl, and n is an integer from 3 to 8, more preferably n is an integer from 3 to 7, and still more preferably n is an integer from 4 to 6.

When R is methyl, these materials are typically referred to as cyclomethicones. Commercially available cyclomethicones include Dow Corning 244 fluid having a viscosity of 2.5 centistokes, and a boiling point of 172° C., which primarily comprises the cyclomethicone tetramer (i. e. n=4), Dow Corning) 344 fluid having a viscosity of 2.5 centistokes and a boiling point of 178° C., which primarily comprises the cyclomethicone pentamer (i. e. n=5), Dow Corning 245 fluid having a viscosity of 4.2 centistokes and a boiling point of 205° C., which primarily comprises a mixture of the cyclomethicone tetramer and pentamer (i. e. n=4 and 5), and Dow Corning's 345 fluid having a viscosity of 4.5 centistokes and a boiling point of 217° C., which primarily comprises a mixture of the cyclomethicone tetramer, pentamer, and hexamer (i. e. n=4, 5, and 6).

Also useful are materials such as commercially available trimethylsiloxysilicate, which is sold as a mixture with dimethicone, as Dow Corning 593 fluid.

Dimethiconols are also suitable for use in the composition. These compounds can be represented by the chemical formula

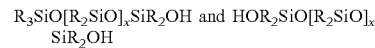

wherein R is an alkyl group (preferably R is methyl or ethyl, more preferably methyl) and x is an integer from 0 to 500, chosen to achieve the desired molecular weight. Commercially available dimethiconols are typically sold as mixtures with dimethicone or cyclomethicone (e. g. Dow Corning 1401, 1402, and 1403 fluids). Polyalkylaryl siloxanes are also suitable for use in the composition.

Preferred for use herein are organopolysiloxanes selected from polyalkylsiloxanes, alkyl substituted dimethicones, cyclomethicones, trimethylsiloxysilicates. dimethiconols, polyalkylaryl siloxanes, and mixtures thereof. More preferred for use herein are polyalkylsiloxanes and cyclomethicones. Preferred among the polyalkylsiloxanes are dimethicones.

Optionally, although preferably, the silicone is a silicone elastomer. Suitable for use herein are silicone elastomers which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Addition reaction-curing organopolysiloxane compositions are preferred for their rapid curing rates and excellent uniformity of curing. A particularly preferred addition reaction-curing organopolysiloxane composition is prepared from: a) an organopolysiloxane having at least 2 lower alkenyl groups in each molecule; b) an organopolysiloxane having at least 2 silicon-bonded hydrogen atoms in each molecule; and c) a platinum-type catalyst.

The compositions of the present invention may include an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomers can notably be chosen from the crosslinked polymers described in U.S. Pat. Nos. 5,412,004, 5,837,793 and 5,811,487. In addition, an emulsifying elastomer comprised of dimethicone copolyol crosspolymer (and) dimethicone is available from Shin Etsu under the tradename KSG-21.

Advantageously, the non-emulsifying elastomers are dimethicone crosspolymers. Such dimethicone crosspolymers are supplied by a variety of suppliers including Dow Corning (EL9240). Other dimethicones corsspolymers are available from General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. Nos. 4,970,252, 5,760,116 and 5,654,362. Commercially available elastomers preferred for use herein are Dow Corning's 9040 silicone elastomer blend, Shin Etsu's KSG-21, and mixtures thereof.

Preferably the oil phase comprises silicone, and most preferably, a silicone elastomer. Preferably, the emulsion composition includes from 20% to 35%, by weight of the emulsion composition, of the silicone elastomer raw material.

The water-in-oil emulsions of the present invention preferably comprise an emulsifier. In a preferred embodiment, the composition comprises from 0.1% to 10% emulsifier, more preferably from 0.25% to 7.5%, still more preferably from 0.5% to 5%, emulsifier by weight of the composition. The emulsifier helps disperse and suspend the aqueous water phase within the preferred silicone oil phase.

Emulsifiers

Suitable emulsifiers include all those suitable for the purpose and known by those skilled in the art for use in skin care products. Preferably these emulsifiers have an HLB value of or less than 14, more preferably from 2 to 14, and still more preferably from 4 to 14.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and chains comprising moieties derived from both ethylene oxide and propylene oxide. Other examples include alkyl-modified dimethicone copolyols, i. e., compounds which comprise C2-C30 pendant side chains. Still other useful dimethicone copolyols include materials having various cationic, anionic, amphoteric and zwitterionic pendant moieties.

The dimethicone copolyol emulsifiers useful herein can be described by the following general structure:

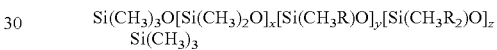
$$Si(CH_3)_3$$

wherein R is C1-C30 straight, branched, or cyclic alkyl and R2 is selected from the group consisting of —(CH$_2$)$_n$—O—(CH$_2$CHR$^3$O) m-H, and —(CH$_2$)$_n$—O—(CH$_2$CHR$^3$O)$_m$—(CH$_2$CHR$^4$O)$_o$—H, wherein n is an integer from 3 to 10; R3 and R4 are selected from the group consisting of H and C1-C6 straight or branched chain alkyl such that R3 and R4 are not simultaneously the same; and m, o, x, and y are selected such that the molecule has an overall molecular weight from 200 to 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the R2 moieties comprising the R3 and R4 groups are not meant to be limiting but are shown as such for convenience.

Also useful herein, although not strictly classified as dimethicone copolyols, are silicone surfactants as depicted in the structures in the previous paragraph wherein R2 is: —(CH$_2$)$_n$—O—R$^5$, wherein R5 is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly (ethylene) (propylene) oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers comprising pendant C2-C30 straight, branched, or cyclic alkyl moieties. A particularly preferred emulsifier is PEG/PPG-18/18 dimethicone.

Suitable, cetyl dimethicone copolyol is commercially available as a mixture with polyglyceryl-4 isostearate (and) hexyl laurate or as a mixture with hexyl laurate and polyglyceryl-3 oleate. Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Among the non-silicone-comprising emulsifiers useful herein are various non-ionic and anionic emulsifying agents such as sugar esters and polyesters, alkoxylated sugar esters and polyesters, Cl-C30 fatty acid esters of C1-C30 fatty alcohols, alkoxylated derivatives of C1-C30 fatty acid esters of C1-C30 fatty alcools, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Non-limiting preferred examples of these non-silicon-comprising emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

Dipeptide

Peptides are defined as compounds comprising an uninterrupted sequence of amino acids. A dipeptide comprises an uninterrupted sequence of two amino acids Amino acids, as employed herein, include and encompass all of the naturally occurring amino acids, either in D or L configuration Amino acids are commonly indicated with reference to the conventional three letter code and the sequence is read from left to right. The emulsions of the present invention comprise a dipeptide selected from the group consisting of acetyl dipeptide 1 cetyl ester, acetyl dipeptide 3 aminohexanoate, azelaoyl bisdipeptide 10, coumaroyl dipeptide 3, dicetyl dipeptide 9, dipeptide diamino butyroyl benzylamide diacetate, dipeptide 1, dipeptide 10, dipeptide 11, dipeptide 12, dipeptide 15, dipeptide 16, dipeptide 17, dipeptide 18, dipeptide 19, dipeptide 2, dipeptide 20, dipeptide 3, dipeptide 4, dipeptide 5, dipeptide 6, dipeptide 7, dipeptide 8, dipeptide 8 HCL, dipeptide 9, hexanoyl dipeptide 3 norleucine acetate, methyl undecylenoyl dipeptide 16, nicotinoyl dipeptide 22, nicotinoyl dipeptide 23, nicotinoyl dipeptide 24, nicotinoyl dipeptide 26, oleoyl dipeptide 15, palmitoyl dipeptide 10, palmitoyl dipeptide 13, palmitoyl dipeptide17, palmitoyl dipeptide 5 diaminobutyroyl hydroxythreonine, palmitoyl dipeptide 5 diaminohydroxybutyrate, palmitoyl dipeptide 7 and mixtures thereof.

More preferably, the emulsions of the present invention comprise a dipeptide wherein said amino acid sequences of said dipeptide are selected from the group consisting of Tyr-Arg, Tyr-Val, Ala-Glu, Val-Trp, Asn-Phe, Asp-Phe and mixtures thereof. More preferably said dipeptide is selected from the group consisting of Trp-Val (tryptophan-valine), Ala-Glu (alanine-glutamine), Tyr-Arg peptide (tyrosine-argenine) and mixtures thereof. Most preferably said dipeptide is N-Acetyl Tyr-Arg-1 cetyl ester.

Dipeptides are preferably incorporated into the emulsion of the present invention at a level of from 0.1 to 50000 ppm, more preferably from 1 to 5000 ppm, most preferably from 10 to 500 ppm.

Other Peptides

In a preferred embodiment of the present invention, the emulsion comprises additional peptides. Preferably said additional peptides are selected from the group consisting of tripeptides, tetrapeptides, pentapeptides and mixtures thereof. By tripeptides, it is meant compound comprising an uninterrupted sequence of three amino acids. By tetrapeptides, it is meant a compound comprising an uninterrupted sequence of four amino acids. By pentapeptide it is meant a compound comprising an uninterrupted sequence of five amino acids.

Tripeptides:

The emulsions of the present invention preferably comprise a tripeptide. Said tripeptide may be naturally occurring or of synthetic origin. Suitable tripeptides include tripeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, derivatives thereof and mixtures thereof.

Particularly preferred tripeptides comprise one or more His-based tripeptides. However another suitable tripeptide may be Arg-Lys-Arg. Particularly preferred tripeptides are based on the structure Gly-His-Lys and its analogs and derivatives thereof. These are collectively known herein as GHK-tripeptides. Indeed, the preferred tripeptide in accordance with this aspect of the invention has this exact sequence of amino acids. Analogs of the preferred tripeptide useful herein include those in which one or more of the three amino acids are reorganized or rearranged within the sequence (e.g., Gly-Lys-His) and/or where no more than two amino acids are substituted (e.g., His-Ala-Orn). However, most preferably, amino acids substituted for Gly include an aliphatic side chain such as, without limitation, beta-Ala, Ala, Val, Leu, Pro, Sarcosine (Sar) and Ile. Most preferred are Ala, Leu and Ile. The most preferable amino acid substituted for Lys or His include those having a side chain that includes, predominantly, a charged nitrogen at a pH of 6, such as, without limitation, Pro, Lys, Arg, His, Desmosine and Isodesmosine. Most preferably, Lys is replaced with Orn, Arg, or Citrulline.

Derivatives are also considered to be encompassed by the term GHK-tripeptides in accordance with the present invention, (and therefore also the more generic term tripeptides). Derivatives of GHK-tripeptides in accordance with the present invention include derivatives of the substituted and rearranged tripeptides described herein. These derivatives include, inter alia, acyl-derivatives, which are tripeptides substituted with one or more straight-chain or branched-chain, long or short chain, saturated or unsaturated, substituted with a hydroxy, amino, acyl amino, sulfate or sulfide group, or unsubstituted, which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid and the like. Preferable examples of the acyl group include an acetyl group, a palmitoyl group, an elaidoyl group, a myristyl group, a biotinyl group and an octanoyl group. These may be substituted or unsubstituted. When substituted, they are preferably substituted with hydroxyl or sulphur comprising groups such as, without limitation SO$_3$H, SH or S—S.

His-based tripeptides include at least one Histadine amine acid. The other two amino acids in the sequence may be the same or different. Thus, contemplated are, without limitation, His-Xaa-Xaa, His-Xaa-Xbb, His-Xbb-Xaa, Xbb-His-Xbb, Xbb-His-Xaa, Xaa-His-Xbb, Xaa-Xaa-His, Xaa-Xbb-His, Xbb-Xaa-His and Xbb-Xbb-His, where Xaa and Xbb are two different amino acids, although either can be His. Preferably, at least one of the other amino acids is Gly, beta-Ala, Ala, Val, Leu, Pro, Sarcosine (Sar) or Ile. Preferably, at least one of the other amino acids is Pro, Lys, Arg, His, Desmosine and Isodesmosine. Most preferably, Lys is replaced with Orn, Arg, or Citrulline.

Derivatives are also considered to be encompassed by the term His-based tripeptides in accordance with the present invention, (and therefore also the more generic term tripeptides). These derivatives include, inter alia, acyl-derivatives, which are tripeptides substituted with one or more straight-chain or branched-chain, long or short chain, saturated or unsaturated substituted or unsubstituted acyl group(s) having from 1 to 29 carbon atoms. The acyl groups which can be used are the same as those described for the GHK-tripeptides.

Particularly preferred embodiments of tripeptides in accordance with the present invention include N-Acyl-Gly-His-Lys and most preferably, N-Palmitoyl-Gly-His-Lys. Preferred commercially available tripeptide and tripeptide derivative compriseing compositions include Biopeptide-CL from SEDERMA, Maxilip® from SEDERMA, Biobustyl® from SEDERMA.

The tripeptides of the present invention are preferably used in amounts that can be as little as 0.10 ppm to 10,000 ppm, preferably between 0.50 ppm to 5,000 ppm, more preferably from 1 ppm to 1000 ppm, and most preferably from 1 ppm to 500 ppm. These are again based on a % w/w basis. Thus 100,000 ppm is 10% by weight of the emulsion.

Tetrapeptides:

The emulsions of the present invention preferably comprise a tetrapeptide. These may be one or more rigin-based tetrapeptides, one or more ALAMCAT-tetrapeptides or mixtures thereof. These tetrapeptides may be naturally occurring or of synthetic origin. Suitable tetrapeptides for use in the present composition include those selected from the group consisting of tetrapeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 34, 35, derivatives thereof and mixtures thereof.

Rigin-based tetrapeptides in accordance with the present invention are based on the structure Gly-Gln-Pro-Arg (SEQ ID NO: 1) (Rigin) and include its analogs and derivatives thereof. Rigin is a preferred tetrapeptide. Analogs of the tetrapeptide rigin useful in accordance with the present invention include those in which one or more of the four amino acids are reorganized or rearranged within the sequence and/or where no more than two of the amino acids are substituted (e.g., Ala-Gln-Thr-Arg (SEQ ID NO: 2). More preferably, at least one of the amino acids within the sequence is Pro or Arg and most preferably the tetrapeptide includes both Pro and Arg although their order and position may vary. The amino acid substitutions can be from amongst any amino acid as defined herein. Particularly preferred rigin-based tetrapeptides include Xaa-Xbb-Arg-Xcc SEQ ID NO: 3), Xaa-Xbb-Xcc-Pro (SEQ ID NO: 4), Xaa-Xbb-Pro-Arg (SEQ ID NO: 5), wherein Xaa-Xbb-Pro-Xcc (SEQ ID NO: 6), Xaa-Xbb-Xcc-Arg (SEQ ID NO: 7), Xaa, Xbb and Xcc may be the same or different and selected from the following Xaa is Gly or the amino acids that may be substituted therefore, Xbb is Gln or the amino acids that may be substituted therefore and Xcc may be Pro or Arg or the amino acids substituted therefore. The most preferable amino acids substituted for Gly include an aliphatic side chain such as, without limitation, beta-Ala, Ala, Val, Leu, Pro, Sarcosine (Sar) and Ile. The most preferable amino acids substituted for Gln include a side chain that includes an amine group that is predominantly uncharged at neutral pH (pH 6-7) such as, without limitation, Asn, Lys, Orn, 5-hydroxyproline, Citrulline and Canavanine. When Arg is substituted, it is preferably replaced with an amino acid having a side chain that includes, predominantly, a charged nitrogen at a pH of 6, such as, without limitation, Pro, Lys, His, Desmosine and Isodesmosine.

Derivatives are also considered to be encompassed by the term rigin-base tetrapeptides in accordance with the present invention, (and therefore also the more generic term tetrapeptides). Derivatives include derivatives of the substituted and rearranged rigin-based tetrapeptides described herein. These derivatives include, inter alia, acyl-derivatives, which are tetrapeptides substituted with one or more straight-chain or branched-chain, long or short chain, saturated or unsaturated, substituted with a hydroxy, amino, amino acyl, sulfate or sulfide group or unsubstituted having from 1 to 29 carbon atoms. N-acyl-derivatives include those acyl groups which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid and the like. Preferable examples of the acyl group include an acetyl group, a palmitoyl group, an elaidoyl group, a myristyl group, a biotinyl group and an octanoyl group. These may be substituted or unsubstituted. When substituted, they are preferably substituted with hydroxyl or sulphur comprising groups such as, without limitation SO3H, SH or S—S.

ALAMCAT tetrapeptides are tetrapeptides which include at least one amino acid including an aliphatic group comprising side chain. These amino acids include, without limitation, Gly, beta-Ala, Ala, Val, Leu, Sarcosine (Sar) and Ile. These tetrapeptides also include at least one amino acid including at least one NH2 comprising side chain. These amino acids include a side chain that has an amine group that is predominantly uncharged at neutral pH (pH 6-7) such as, without limitation, Gln, Asn, Lys, Orn, 5-hydroxyproline, Citrulline and Canavanine The ALAMCAT-tetrapeptides also include at least one amino acid having at least one side chain including at least one cationic amine (predominant species is charged such as NH3+, NH2+, etc.—basic amino acids which are positively charged at pH 6.0). These amino acids include, without limitation, Pro, Arg, Lys, His, Desmosine and Isodesmosine. The remaining amino acid can be any amino acid, but is preferably one comprising an alphatic group, pendant amino group or pendant cationic group.

Derivatives are also considered to be encompassed by the term ALAMCAT-tetrapeptides in accordance with the present invention, (and therefore also the more generic term tetrapeptides). These derivatives include, inter alia, acyl-derivatives, which are tetrapeptides substituted with one or more straight-chain or branched-chain, substituted or unsubstituted long or short chain, saturated or unsaturated acyl group(s) having from 1 to 29 carbon atoms. The acyl groups which can be used are the same as those described for the rigin-based tetrapeptides.

Preferred embodiments include Peptide E, arg-ser-arg-lys (SEQ ID NO: 8), N-acyl-Gly-Gln-Pro-Arg (SEQ ID NO: 9) peptides, most preferably N-palmitoyl-Gly-Gln-Pro-Arg (SEQ ID NO: 10).

Preferred commercially available sources of tetrapeptides include RIGIN, EYELISS, Haloxyl, and MATRIXYL 3000, which comprise between 50 to 500 ppm of palmitoyl-Gly-Gln-Pro-Arg, and other ingredients, such as peptides, chalcones and an excipient, commercially available from SEDERMA, France. Tego Pep 417 available from Evonik. These may be used to produce compositions of the present invention by adding thereto at least one tripeptide as described herein.

The tetrapeptides of the present invention are preferably used in amounts from 0.1 ppm (0.00001% w/w also referred to herein as "weight percent", "weight %" or simply by weight) to 10,000 ppm (0.5% w/w), preferably from 0.5 ppm to 1000 ppm (0.05% w/w), and most preferably from 1 ppm to 500 ppm by weight of the composition.

The combination of tripeptides and tetrapeptides, is particularly preferred. The preferred ratio of tetrapeptide to tripeptide, or indeed the ratio of molecules having four amino acids to those having three amino acids can range from 100:1 to 1:100; more preferably from 50:1 to 1:50, even more preferably from 30:1 to 1:30 and even more preferably between 10:1 to 1:10. Most preferably, the ratio of tetrapeptide to tripeptide ranges from between 3:1 to 1:3. These ratios are on a weight basis (% w/w-e.g. mg of pure peptide per Kilogram in the final formulation). In a particularly preferred embodiment, the amount of tripeptide used is greater than the amount of tetrapeptide used when considered in terms of their amounts in parts per million, again based on overall weight of the composition. In a particularly preferred embodiment, the emulsion of the present invention comprise a tetrapeptide of the sequence Gly-Gln-Pro-Arg (SEQ ID NO: 1), its analogs and derivatives in combination with one or more tripeptide of the sequences Gly-His-Lys, its analogs and derivatives.

Pentapeptides

The compositions of the present invention may optionally comprise a pentapeptide, derivatives of pentapeptides, and mixtures thereof. As used herein, "pentapeptides" refers to both the naturally occurring pentapeptides and synthesized pentapeptides. Also useful herein are naturally occurring and commercially available compositions that comprise pentapeptides. Suitable pentapeptides are those selected from the group consisting of pentapeptide1, 4, 5, 6, 7, 8, 9, 10, 11, 12, 13, 14, 15, 16, 17, 18, 19, 21, 22, 23, 24, 25, 26, 28, 29, 30, 31, 33, 34, 35, 36, 38, 39, derivatives thereof and mixtures thereof.

Suitable pentapeptides for use herein are the pentapeptide, lys-thr-thr-lys-ser (SEQ ID NO: 12), Arg-asp-lys-tyr-val (SEQ ID NO: 13) (pentapeptide -1) and derivatives thereof. A preferred commercially available pentapeptide derivative-comprising composition is Matrixyl which comprises 100 ppm of palmitoyl-lys-thr-thr-lys-ser (SEQ ID NO: 14) and is commercially available from Sederma, France.

The pentapeptides and/or pentapeptide derivatives where present are preferably included in emulsion at amounts of from 0.01% to 20%, more preferably from 0.05% to 15%, and even more preferably from 0.1% to 10%, by weight of the emulsion composition.

Matrix Metalloproteinase Inhibitors (MMPi)

The term "matrix metalloproteinase inhibitor" relates to all molecule and/or plant or bacterial extracts having an inhibitory activity on at least one of the matrix metalloproteinases expressed or synthetized by or in the skin. The family of the matrix metalloproteinases is formed of several well-defined groups on the basis of their resemblance regarding structure and substrate specificity (Woessner J. F., Faseb Journal, vol. 5, 1991, 2145). Among these groups, there are collagenases able to degrade fibrillar collagens (MMP-1 or interstitial collagenase, MMP-8 or neutrophil collagenase, MMP-13 or collagenase 3, MMP-18 or collagenase 4), gelatinases degrading type IV collagen or other denatured collagen form (MMP-2 or A gelatinase (72 kDa), MMP-9 or B gelatinase (92 kDa)), stromelysins (MMP-3 or stromelysin 1, MMP-10 or stromelysin 2, MMP-11 or stromelysin 3) whose broad spectrum of activity targets proteins of the extracellular matrix such as glycoproteins (fibronectin, laminin), proteoglycanes etc., matrilysin (MMP-7), metalloelastase (MMP-12) or metalloproteinases (MMP-14, MMP-15, MMP-16 and MMP-17). Metalloproteinases (MMPs) are proteases that use a metal, (mostly zinc) coordinated to 3 cystein residues and to a methionine in their active site, that degrade macromolecular components of the extracellular matrix and of basal layers at neutral pH (collagen, elastin, etc. . . . ). This group of enzymes is inactivated by metal chelators. The principal activity regulators of MMPs are the tissue inhibitors of metalloproteinases or TIMPs such TIMP-I, TIMP-2, TIMP-3 and TIMP-4 (Woessner J. F., Faseb Journal, 1991). Furthermore, the MMPs expression is also regulated by growth factors, cytokins, oncogens products (ras, jun), or also matrix constituents.

The term "matrix metalloproteinase inhibitors" according to the present invention means all molecules able to reduce the MMPs activity regarding the gene expression (transcription and translation) or regarding the activation of the zymogen form of MMPs, or else regarding the local control of active forms. Furthermore, the metalloproteinase inhibitors according to the present invention can also be MMP-1 inhibitors of natural or synthetic origin. The terms "natural origin" or "synthetic origin" mean both a metalloproteinase inhibitor at a pure state or in solution at different concentrations, but natural origin termed inhibitors are obtained by different extraction methods from a natural element (for example lycopene from a tomato) whereas the inhibitors of synthetic origin are all obtained via chemical synthesis Preferred MMPi are selected from the group consisting of retinoid, N-acetyl cysteine, glutathione, 2-furildioxime, vitamin C, flavones, isoflavones, hydrolysed rice protein, alfalfa extract, white lupin, zizyphus jujube extract, dihydroxy methyl chromone, kudzu extract, *vitis vinifera* extract, *Oenothera biennis* extract *Anogeissus leiocarpus* extract and mixtures thereof.

Where present MMPi are present at a level of from 0.01% to 10%, more preferably 0.1% to 5% and most preferably from 1% to 2.5% by weight of the emulsion.

Skin Conditioning Agent

The emulsion of the present invention may optionally comprise a skin conditioning agent. Said skin conditioning agents may preferably be selected from the group consisting of humectants, emollients, moisturisers, or mixtures thereof. Where present, they are preferably present at a level of from 0.01% to 20%, more preferably from 0.1% to 10%, most preferably from 0.5% to 7% by weight of the emulsion.

Preferred skin conditioning agents are selected from the group consisting of guanidine, urea, glycolic acid and glycolate salts, salicylic acid, lactic acid and lactate salts, aloe vera, shea butter, polyhydroxy alcohols, such as sorbitol, mannitol, xylitol, erythritol, glycerol, hexanetriol, butanitriol, (di) propylene glycol, butylene glycol, hexylene glycol, polyethylene glycol, sugars (e.g. fructose, glucose, xylose, honey, mannose, xylose), gluconodeltalactone, and starches and their derivatives, pyrrolidone, carboxylic acid, hyaluronic acid and salts thereof, lactamide monoethanolamine, acetamide monoethanolamine, panthenol, allantoin and mixtures thereof.

More preferably said skin conditioning agent is selected from glycerine, arabinoglactan, butylene glycol, hyaluronic acid, shea butter, propylene glycol, ethylhexyl glycerin and hyaluronate.

Antioxidant Agent

The emulsion of the present invention may optionally comprise an antioxidant agent. Suitable antioxidant agents may include: a) ascorbic acid its salts, esters, glucosides and glucosamines, particularly sodium ascorbyl phosphate, magnesium ascorbyl phosphate and ascorbyl palmitate b) vitamin E (tocopherol) and its esters, particularly tocopheryl acetate, as well as Dimethyl methoxy chromanol which is a synthetic analogue of gamma tocopherol, available from Lipotec S.A. polygon Industrial Camri Ral, under the tradename Lipochroman-6 c) herbal extracts, particularly *gingko biloba*, such as that available under the trade name "Gingko Biloba Leaf Powder" from Univar PLC, *morus alba*, such as that available under the trade name "Mulberry Concentrate" from Solabia, *origanum vulgare*, such as that available under the trade name "Pronalen *Origanum* HSC" from S Black Ltd, *panax ginseng*, such as that available under the trade name "*Panax ginseng* 1.1 extract 4294" from S Black Ltd or "Phytexcell *Panax ginseng*" available from Croda Chemicals Ltd, birch extract such as those available from Cosmetochem (U. K.) Ltd under the trade names "Super Herbasol Extract Birch" and "HP Herbasol *Betula*" and those available from Blagden Chemicals under the tradenames "Phytelene of Birch" and "Aqueous Spray Dried Birch", *camellia sinensis*, such as that available under the trade name "Herbal Extract Green Tea 75% Solids" from Nichimen Europe, *rosmarrinus officinalis*, such as that available under the trade name "Pronalen Rosemary" from S. Black, Acerola cherry powder, such as that available as Acerola PE from Gee Lawson, Emlica extract sold under the tradename Emblica™ by Merck Speciality chemicals, and Grape Seed oil, such as that available from Chesham Chemicals Limited.

The source of the antioxidant activity in some of these agents is often not fully understood; for example, it is believed that the antioxidant activity of ginkgo biloba extract arises from the presence of flavonglycocides and/or terpenelactones which may be free-radical inhibitors. Birch extract may be produced by extracting the dried leaves of *Betula alba* with a suitable solvent. It is believed that the anti-free radical activity of birch extract arises due to the presence of flavonoids such as hyperosid, quencitrosid and/or myricetol-3digalactosid which may be free-radical inhibitors. Such products are then often sold as mixtures or solutions.

Thus the antioxidant agent may consist of a number of active ingredients which are free-radical inhibitors or may also comprise suitable diluents and/or carriers (such as when the anti-free radical agent is some of the products mentioned herein). Thus there may be some confusion as to the actual level of agent within a commercially available product. Accordingly, the amounts of antioxidant agents used in the present invention are expressed as dry weights, as understood by a man skilled in the art. The total amount of antioxidant agents present in the composition may range from 0.005% to 10% by weight, preferably 0.5% to 5%, most preferably 1% to 3.5% by weight of the composition.

Particularly preferred synergistic combinations of antioxidant agents suitable for inclusion in a skin care composition of the present invention are: *panax ginseng, morus alba* and magnesium ascorbyl phosphate; *panax ginseng, morus alba* and sodium ascorbyl phosphate; *panax ginseng, morus alba* and *rosmarinus officinalis; panax ginseng, morus alba* and *origanum vulgare.*

In these preferred combinations (a) the *panax ginseng* is preferably present in an amount of 0.005% to 0.1%, more preferably 0.01% to 0.05% by weight of the composition; (b) the *morus alba* is preferably present in an amount of 0.0005% to 0.01%, more preferably 0.001% to 0.005% by weight of the composition; (c) the sodium or magnesium ascorbyl phosphate is preferably present in an amount of 0.05% to 2.5%, preferably 0.1% to 2%, most preferably 0.15% to 1.5% by weight of the composition and (d) the *rosmarinus officinalis* or *origanum vulgare* is preferably present in an amount of 0.01% to 0.5%, more preferably 0.05% to 0.2% by weight of the composition.

Vitamins

The compositions of the present invention may comprise one or more vitamins. The emulsion compositions may comprise ascorbates, for example vitamin C, vitamin C derivatives, ascorbic acid, ascorbyl glucoside, ascorbyl palmitate, magnesium ascorbyl phosphate, sodium ascorbyl phosphate. The emulsion may comprise vitamin B, vitamin B derivatives, vitamin B1 to vitamin B 12 and theirs derivatives, vitamin K, vitamin K derivatives, vitamin H vitamin D, vitamin D derivatives, vitamin E, vitamin E derivatives such as tocopherol and tocopheryl acetate, and provitamins thereof, such as panthenol and mixtures thereof. The vitamin compounds may be included as the substantially pure material, or as an extract obtained by suitable physical and/or chemical isolation from natural (e. g., plant) sources. In one embodiment, when vitamin compounds are present in the compositions of the instant invention, the emulsion compositions comprise from about 0.0001% to 50%, more preferably from 0.001% to 10%, still more preferably from 0.01% to 8%, and still more preferably from 0.1% to 5%, by weight of the composition, of the vitamin compound.

Salicylic Acid Compound

The emulsion compositions of the present invention may comprise a salicylic acid compound, its esters, its salts, or combinations thereof. In one embodiment of the compositions of the present invention, the salicylic acid compound preferably comprises from 0.0001% to 25%, more preferably from 0.001% to 15%, even more preferably from 0.01% to 10%, still more preferably from 0.1% to 5%, and even more preferably from 0.01% to 2%, by weight of the composition, of salicylic acid.

Sunscreen

The emulsions of the present invention may optionally comprise a sunscreen component. The sunscreen may comprise organic or inorganic sun filters or a combination of the two. Suitable inorganic sunfilters include those selected from the group consisting of microfine titanium dioxide, microfine zinc oxide, boron nitride and mixtures thereof.

Suitable organic sunscreens include those selected from the group consisting of: a) p-aminobenzoic acids, their esters and derivatives (for example, 2ethylhexyl p-dimethylaminobenzoate), b) methoxycinnamate esters (for example, 2-ethylhexyl p-methoxycinnamate, 2-ethoxyethyl p-methoxycinnamate or a, p-di-(p-methoxycinnamoyl)-a'-(2ethylhexanoyl)-glycerin, c) benzophenones (for example oxybenzone), d) dibenzoylmethanes such as 4-(tert-butyl)-4'-methoxydibenzoylmethane, e) 2-phenylbenzimidazole-5 sulfonic acid and its salts, f) alkyl-ss, ss-diphenylacrylates for example alkyl a-cyano-ss, ss-diphenylacrylates such as octocrylene, g) triazines such as 2,4,6-trianilino-(p-carbo-2-ethyl-hexyl-1-oxi)-1, 3,5 triazine, h) camphor derivatives such as methylbenzylidene camphor and i) mixtures thereof. Other preferred sunscreen ingredients include those selected from the group consisting of homosalate, Ethylhexyl salicylate, Diethylhexylbutamido triazone, Bis-ethylhexyloxyphenol methoxyphenyl triazine, Diethylamino hydroxybenzoyl hexyl benzoate, Butyl methoxydibenzoylmethane, Methylene bis-benzotriazoyl tetramethylbutylphenol, Polysilicone-15 and mixtures thereof. A sunscreening agent is optionally present in an amount from 0.1 to 10% by weight of the composition.

Other Optional Ingredients

The emulsions of the present invention may also optionally comprise one or more of the following optional ingredients. Preservatives may be added to the emulsion such as 2-bromo2-nitropropane-1,3-diol (bronopol, which is available commercially under the trade name Myacide®), benzyl alcohol, diazolidinyl urea, imidazolidinyl urea, methyl paraben, phenoxy ethanol, ethyl paraben, propyl paraben, sodium methyl paraben, sodium dehydroacetate, polyhexamethylenebiguanide hydrochloride, isothiazolone and sodium propyl paraben, suitably in an amount of from 0.01% to 10% by weight of the emulsion.

Thickeners, viscosity modifying agents and/or gelling agents may be added to the emulsion composition, such as acrylic acid polymers e. g. available commercially under the trade name Carbopol or Ultrez (Lubrizol) or modified celluloses e. g. hydroxyethylcellulose available commercially under the trade name Natrosol (Hercules) or hydroxypropylmethyl cellulose, amine oxides, block polymers of ethylene oxide and propylene oxide (for example, those available from BASF Wyandotte under the trade name "Pluronic"®), PVM, MA, or a decadiene crosspolymer (available under the trade name Stabilez 60), ethoxylated fatty alcohols, salt (magnesium chloride, sodium chloride), Aristoflex AVC (Clariant), phthalic acid amide, xanthan gum, sodium polyacrylate, polyvinyl alcools, fatty alcools and alkyl galactmanans available under the trade name N-Hance from Hercules, suitably in an amount of from 0.5% to 10% by weight of the composition.

Sequestering agents may be added to the emulsion composition, such as ethylenediamine tetraacetic acid and salts thereof, suitably in an amount of from 0.005% to 0.5% by weight of the composition.

The emulsion composition may also include waxes such as cocoa butter suitably in an amount of from 1% to 99% by weight of the composition.

The emulsion composition may also comprise suitable, cosmetically acceptable diluents, carriers and/or propellants such as dimethyl ether.

The emulsion composition may also include pearlising agents such as stearic monoethanolamide and/or mica, suitably in an amount of from 0.01% to 10% by weight of the composition.

Perfumes may be added suitably in an amount of from 0.01% to 2% by weight of the composition, as may water soluble dyes such as tartrazine, suitably in an amount of from a trace amount (such as 1×10-5%) to 0.1% by weight of the composition.

The emulsion composition may also include pH adjusting agents such as sodium hydroxide, aminomethyl propanol, triethanolamine, suitably in an amount of from 0.01% to 10% by weight of the composition. The composition may be buffered by means well known in the art, for example by use of buffer systems comprising succinic acid, citric acid, lactic acid, and acceptable salts thereof, phosphoric acid, mono- or disodium phosphate and sodium carbonate. Suitably, the composition may have a pH between 3 and 10, preferably between 4 and 8.

EXAMPLES

The skin permeation of dipeptides was measured in vitro using Franz diffusion cells. A Franz cell chamber is a recognised in vitro skin permeation assay to determine the degree of permeation of a given product into or through the skin. The Franz cell apparatus consists of two primary chambers separated by a membrane. The membrane in the present experiment was excised porcine skin samples, placed between the Franz cell chambers, with an effective diffusion diameter of 0.9 cm. The receptor compartment had a volume of 4.2 ml and was filled with receptor fluid consisting of 20% ethanol in water. Throughout the experiment, the receptor chamber content was continuously agitated by a small magnetic stirrer. The temperature of the skin was maintained at 32° C. by a water circulating system regulated at 37° C. The donor chamber was open to the atmosphere. 200 ml of the test compositions containing an identical peptide concentration were evenly applied to the skin in the donor chamber side of individual cells using a smooth spatula.

|  | Water in oil emulsion wt % | Oil in water emulsion wt % |
|---|---|---|
| Dimethicone | 13.83 | 2.00 |
| Water | 42.14 | 79.84 |
| Glycerin | 5.01 | 5.01 |
| Dimethicone crosspolymer | 32.31 | 1.00 |
| Butylene glyccol | 2.59 | — |
| PEG/PPG-18/18 dimethicone & Polyglyceryl-4 isostearate & Hexyl laurate blend | 1.00 | — |
| Magnesium sulphate | 0.6 | — |
| Phenoxyethanol & Methylparaben & Ethylparaben | 0.55 | 0.80 |
| Glyceryl Stearate &7 PEG 100 Stearate | — | 2.00 |
| Cetearyl alcohol | — | 2.00 |
| Sodium polyacrylate | — | 0.6 |
| Xanthan gum | — | 0.1 |
| EDTA & sodium Hydroxide | — | 0.05 |
| Acetyl dipeptide 1 cetyl ester | 0.0046 | 0.0046 |
| Palmitoyl oligopeptide | 0.0018 | 0.0018 |
| Palmitoyl tetrapeptide 7 | 0.0009 | 0.0009 |

After 24 hours, skin sample dissection was carried out. First, the remainder of the test formulation was collected by scraping the dried composition from the skin surface with a spatula. Then, the upper skin surface was removed by removing 10 sequential tape strips using D-Squame disks (CuDerm Corp, Dallas Tex., USA). The rest of epidermis and dermis was extracted with acetonitrile for 3 hours and the product thereof analysed using Accurate Mass Spectrometry. The experiments were repeated 6 times for each formulation base, providing the below results.

| | Dipeptide peak Intensity Counts | |
|---|---|---|
| Repeat | Water in oil emulsion | Oil in water emulsion |
| 1 | 2,900,532 | 892,069 |
| 2 | 4,031,113 | 1,346,387 |

-continued

| Dipeptide peak Intensity Counts | | | |
|---|---|---|---|
| Repeat | Water in oil emulsion | Oil in water emulsion | |
| 3 | 4,767,149 | 1,596,184 | |
| 4 | 3,047,682 | 1,252,019 | |
| 5 | 4,194,807 | 1,224,843 | |
| 6 | 5,300,533 | 1,012,254 | |
|  | 4,040,302 | 1,220,626 | Mean Intensity |

The above data clearly shows the improved skin penetration of dipeptide when using a water in oil emulsion of the present invention, as opposed to the more standard moisturiser composition, of oil in water. The above data is also represented in FIG. 1.

The present represent non-binding example of water-in-oil emulsions of the present invention.

| Water-in-oil emulsion 1 | |
|---|---|
| Dimethicone | 23.744 |
| Aqua | 35 |
| Dimethicone crosspolymer and Dimethicone | 25 |
| Glycerin | 5 |
| PEG/PPG-18/18 dimethicone | 3 |
| Cetyl PEG/PPG-10/1 dimethicone | 2 |
| Magnesium sulfate | 0.75 |
| Phenoxyethanol | 0.7 |
| Methylparaben | 0.2 |
| Ethylparaben | 0.1 |
| Aceyl dipeptide-1 cetyl ester | 0.005 |
| Palmitoyl oligopeptide and Palmitoyl tetrapeptide-7 | 0.001 |
| Sodium hyaluronate | 0.5 |
| Hydrolyzed rice protein | 2 |
| Alfalfa extract | 2 |

Method of Manufacture
1. In the main vessel combine Dimethicone, Dimethicone crosspolymer, PEG/PPG-18/18 dimethicone and Cetyl PEG/PPG-10/1 dimethicone to prepare the oil phase.
2. Separately weigh out water, magnesium sulphate, glycerin, Aceyl dipeptide-1 cetyl ester, Palmitoyl oligopeptide and Palmitoyl tetrapeptide-7, Sodium hyaluronate, Hydrolyzed rice protein and Alfalfa extract, stir until solids are dissolved, preparing the water phase.
3. Separately mix together phenoxyethanol, methylparaben and ethylparaben. Heat until dissolved and add to the water phase (of step 2)
4. Add the water phase to the oil phase slowly with constant stirring at high speed (creating a vortex). Continue stirring for 5 minutes.
5. Homogenise the product for 5 minutes at 3500 rpm using a Silverson mixer or equivalent.

| Water-in-oil emulsion 2 | |
|---|---|
| Dimethicone | 38.744 |
| Aqua | 20 |
| Dimethicone crosspolymer and Dimethicone | 25 |
| Glycerin | 5 |
| PEG/PPG-18/18 dimethicone | 3 |
| Cetyl PEG/PPG-10/1 dimethicone | 2 |
| Magnesium sulfate | 0.75 |
| Phenoxyethanol | 0.7 |
| Methylparaben | 0.2 |
| Ethylparaben | 0.1 |
| Aceyl dipeptide-1 cetyl ester | 0.005 |
| Palmitoyl oligopeptide and Palmitoyl tetrapeptide-7 | 0.001 |
| Sodium hyaluronate | 0.5 |
| Hydrolyzed rice protein | 2 |
| Alfalfa extract | 2 |

Method of Manufacture
1. In the main vessel add Dimethicone, Dimethicone crosspolymer, PEG/PPG-18/18 dimethicone and Cetyl PEG/PPG-10/1 dimethicone to make the oil phase.
2. Separately weigh out water, magnesium sulphate, glycerin, Aceyl dipeptide-1 cetyl ester, Palmitoyl oligopeptide and Palmitoyl tetrapeptide-7, Sodium hyaluronate, Hydrolyzed rice protein and Alfalfa extract, stir until solids are dissolved to make the water phase.
3. Separately mix together phenoxyethanol, methylparaben and ethylparaben. Heat until dissolved and add to the water phase (of step 2)
4. Add the water phase to the oil phase slowly with constant stirring at high speed (creating a vortex). Continue stirring for 5 minutes.
5. Homogenise the product for 5 minutes at 3500 rpm using a Silverson mixer or equivalent.

| Water-in-oil emulsion 3 | |
|---|---|
| Dimethicone | 8.744 |
| Aqua | 50 |
| Dimethicone crosspolymer and Dimethicone | 25 |
| Glycerin | 5 |
| PEG/PPG-18/18 dimethicone | 3 |
| Cetyl PEG/PPG-10/1 dimethicone | 2 |
| Magnesium sulfate | 0.75 |
| Phenoxyethanol | 0.7 |
| Methylparaben | 0.2 |
| Ethylparaben | 0.1 |
| Aceyl dipeptide-1 cetyl ester | 0.005 |
| Palmitoyl oligopeptide and Palmitoyl tetrapeptide-7 | 0.001 |
| Sodium hyaluronate | 0.5 |
| Hydrolyzed rice protein | 2 |
| Alfalfa extract | 2 |

Method of Manufacture
1. In the main vessel add Dimethicone, Dimethicone crosspolymer, PEG/PPG-18/18 dimethicone and Cetyl PEG/PPG-10/1 dimethicone to make the oil phase.
2. Separately weigh out water, magnesium sulphate, glycerin, Aceyl dipeptide-1 cetyl ester, Palmitoyl oligopeptide and Palmitoyl tetrapeptide-7, Sodium hyaluronate, Hydrolyzed rice protein and Alfalfa extract, stir until solids are dissolved and the water phase is prepared.
3. Separately mix together phenoxyethanol, methylparaben and ethylparaben. Heat until dissolved and add to the water phase (of step 2)
4. Add the water phase to the oil phase slowly with constant stirring at high speed (creating a vortex) Continue stirring for 5 minutes.
5. Homogenise the product for 5 minutes at 3500 rpm using a Silverson mixer or equivalent.

| Water-in-oil emulsion 4 | |
|---|---|
| Dimethicone | 23.744 |
| Aqua | 33.5 |
| Dimethicone crosspolymer and Dimethicone | 25 |
| Glycerin | 5 |
| PEG/PPG-18/18 dimethicone | 3 |
| Cetyl PEG/PPG-10/1 dimethicone | 2 |
| Magnesium sulphate | 0.75 |
| Phenoxyethanol | 0.7 |
| Methylparaben | 0.2 |
| Ethylparaben | 0.1 |
| Aceyl dipeptide-1 cetyl ester | 0.005 |
| Palmitoyl oligopeptide and Palmitoyl tetrapeptide-7 | 0.001 |
| Butylene glycol | 2 |
| Hydrolyzed rice protein | 2 |
| Alfalfa extract | 2 |

Method of Manufacture
1. In the main vessel add Dimethicone, Dimethicone crosspolymer, PEG/PPG-18/18 dimethicone and Cetyl PEG/PPG-10/1 dimethicone to make the oil phase.
2. Separately weigh out water, magnesium sulphate, glycerin, Aceyl dipeptide-1 cetyl ester, Palmitoyl oligopeptide and Palmitoyl tetrapeptide-7, Butylene glycol, Hydrolyzed rice protein and Alfalfa extract, stir until solids are dissolved to make the water phase.
3. Separately mix together phenoxyethanol, methylparaben and ethylparaben. Heat until dissolved and add to the water phase (of step 2)
4. Add the water phase to the oil phase slowly with constant stirring at high speed (creating a vortex). Continue stirring for 5 minutes.
5. Homogenise the product for 5 minutes at 3500 rpm using a Silverson mixer or equivalent.

| Water-in-oil emulsion 5 | |
|---|---|
| Dimethicone | 27.744 |
| Aqua | 40 |
| Dimethicone crosspolymer and Dimethicone | 20 |
| Glycerin | 5 |
| PEG/PPG-18/18 dimethicone | 3 |
| Cetyl PEG/PPG-10/1 dimethicone | 2 |
| Magnesium sulphate | 0.75 |
| Phenoxyethanol | 0.7 |
| Methylparaben | 0.2 |
| Ethylparaben | 0.1 |
| Aceyl dipeptide-1 cetyl ester | 0.005 |
| Palmitoyl oligopeptide and Palmitoyl tetrapeptide-7 | 0.001 |
| Sodium hyaluronate | 0.5 |

Method of Manufacture
1. In the main vessel add Dimethicone, Dimethicone crosspolymer, PEG/PPG-18/18 dimethicone and Cetyl PEG/PPG-10/1 dimethicone to make the oil phase.
2. Separately weigh out water, magnesium sulphate, glycerin, Aceyl dipeptide-1 cetyl ester, Palmitoyl oligopeptide and Palmitoyl tetrapeptide-7 and Sodium hyaluronate, stir until solids are dissolved to make the water phase.
3. Separately mix together phenoxyethanol, methylparaben and ethylparaben. Heat until dissolved and add to the water phase (of step 2)
4. Add the water phase to the oil phase slowly with constant stirring at high speed (creating a vortex). Continue stirring for 5 minutes.
5. Homogenise the product for 5 minutes at 3500 rpm using a Silverson mixer or equivalent.

The invention claimed is:

1. A water-in-oil emulsion comprising an oil phase and a water phase, and wherein the water phase comprises a dipeptide selected from the group consisting of acetyl dipeptide 1 cetyl ester, acetyl dipeptide 3 aminohexanoate, azelaoyl bisdipeptide 10, coumaroyl dipeptide 3, dicetyl dipeptide 9, dipeptide diamino butyroyl benzylamide diacetate, dipeptide 1, dipeptide 10, dipeptide 11, dipeptide 12, dipeptide 15, dipeptide 16, dipeptide 17, dipeptide 18, dipeptide 19, dipeptide 2, dipeptide 20, dipeptide 3, dipeptide 4, dipeptide 5, dipeptide 6, dipeptide 7, dipeptide 8, dipeptide 8 HCL, dipeptide 9, hexanoyl dipeptide 3norleucine acetate, methyl undecylenoyl dipeptide 16, nicotinoyl dipeptide 22, nicotinoyl dipeptide 23, nicotinoyl dipeptide 24, nicotinoyl dipeptide 26, oleoyl dipeptide 15, palmitoyl dipeptide 10, palmitoyl dipeptide 13, palmitoyl dipeptide 17, palmitoyl dipeptide 5 diaminobutyroyl hydroxythreonine, palmitoyl dipeptide 5 diaminohydroxybutyrate, palmitoyl dipeptide 7 and mixtures thereof, and a further peptide selected from the group consisting of tripeptide, tetrapeptide, pentapeptide and mixtures thereof, and wherein the water phase is present as a minor phase and wherein water is present in the emulsion in amount greater than or equal to 35% but less than 45%.

2. A water in oil emulsion according to claim 1 wherein the dipeptide is selected from those comprising amino acid sequence, Tyr-Arg, Tyr-Val, Ala-Glu, Val-Trp, Asn-Phe, Asp-Phe and mixtures thereof.

3. An emulsion according to claim 1 wherein the dipeptide is present at a level of 0.1 to 10000 ppm.

4. An emulsion according to claim 1 wherein the dipeptide comprises amino acid sequence Tyr-Arg.

5. An emulsion according to claim 4, wherein the further peptide is selected from the group consisting of tripeptide, tetrapeptide and mixtures thereof.

6. An emulsion according to claim 1 further comprising hyaluronic acid or salt thereof.

7. An emulsion according to claim 1 further comprising a matrix metalloproteinase inhibitor (MMPi).

8. An emulsion according to claim 7, wherein the MMPi is selected from the group consisting of retinoid, N-acetyl cysteine, glutathione, 2-furildioxime, vitamin C, flavones, isoflavones, hydrolysed rice protein, alfalfa extract, white lupin, zizyphus jujube extract, dihydroxy methyl chromone, kudzu extract, vitis vinifera extract, Oenothera biennis extract Anogeissus leiocarpus extract and mixtures thereof.

9. An emulsion according to claim 1 wherein the oil phase comprises a silicone comprising compound.

10. A method of treating mammalian skin comprising:
topically applying an emulsion according to claim 1 to the skin of a mammal in need of skin care treatment.

11. An emulsion according to claim 1 wherein the dipeptide is present at a level of 1 to 1000 ppm by weight of the emulsion.

12. An emulsion according to claim 1 wherein the dipeptide is N-Acetyl Tyr-Arg-1 cetyl ester.

13. An emulsion according to claim 9 wherein the silicone comprising compound is selected from the group consisting of dimethicone, dimethyl siloxane, silicone elastomer and mixtures thereof.

14. An emulsion according to claim 1, wherein the water phase comprises acetyl dipeptide 1 cetyl ester and a palmitoyl tetrapeptide and the oil phase comprises dimethicone, a silicone elastomer, and a silicone emulsifier.

15. An emulsion according to claim 14, wherein the acetyl dipeptide 1 cetyl ester is present in the emulsion at a level of 1 ppm to 5000 ppm and the palmitoyl tetrapeptide is present in the emulsion at a level of 1 ppm to 10000 ppm.

16. An emulsion according to claim 15, wherein the emulsion comprises from 20 weight % to 35 weight % of the silicone elastomer and 0.5 weight % to 10 weight % of the silicone emulsifier.

* * * * *

SEQUENCE LISTING

```
<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 1

Gly Gln Pro Arg
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 2

Ala Gln Thr Arg
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
```

<221> NAME/KEY: MISC_FEATURE
<222> LOCATION: (1)..(1)
<223> OTHER INFORMATION: Gly or the amino acids that may be substituted
      therefore
<220> FEATURE:
<221> NAME/KEY: MISC_FEATURE
<222> LOCATION: (2)..(2)
<223> OTHER INFORMATION: Gln or the amino acids that may be substituted
      therefore
<220> FEATURE:
<221> NAME/KEY: MISC_FEATURE
<222> LOCATION: (4)..(4)
<223> OTHER INFORMATION: Pro or Arg or the amino acids substituted
      therefore

<400> SEQUENCE: 3

Xaa Xaa Arg Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Gly or the amino acids that may be substituted
      therefore
<220> FEATURE:
<221> NAME/KEY: MISC_FEATURE
<222> LOCATION: (2)..(2)
<223> OTHER INFORMATION: Gln or the amino acids that may be substituted
      therefore
<220> FEATURE:
<221> NAME/KEY: MISC_FEATURE
<222> LOCATION: (3)..(3)
<223> OTHER INFORMATION: Pro or Arg or the amino acids substituted
      therefore

<400> SEQUENCE: 4

Xaa Xaa Xaa Pro
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Gly or the amino acids that may be substituted
      therefore
<220> FEATURE:
<221> NAME/KEY: MISC_FEATURE
<222> LOCATION: (2)..(2)
<223> OTHER INFORMATION: Gln or the amino acids that may be substituted
      therefore

<400> SEQUENCE: 5

Xaa Xaa Pro Arg
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: MISC_FEATURE
<222> LOCATION: (1)..(1)
<223> OTHER INFORMATION: Gly or the amino acids that may be substituted
      therefore
<220> FEATURE:
<221> NAME/KEY: MISC_FEATURE
<222> LOCATION: (2)..(2)
<223> OTHER INFORMATION: Gln or the amino acids that may be substituted
      therefore
<220> FEATURE:
<221> NAME/KEY: MISC_FEATURE
<222> LOCATION: (4)..(4)
<223> OTHER INFORMATION: Pro or Arg or the amino acids substituted
      therefore

<400> SEQUENCE: 6

Xaa Xaa Pro Xaa
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Gly or the amino acids that may be substituted
      therefore
<220> FEATURE:
<221> NAME/KEY: MISC_FEATURE
<222> LOCATION: (2)..(2)
<223> OTHER INFORMATION: Gln or the amino acids that may be substituted
      therefore
<220> FEATURE:
<221> NAME/KEY: MISC_FEATURE
<222> LOCATION: (3)..(3)
<223> OTHER INFORMATION: Pro or Arg or the amino acids substituted
      therefore

<400> SEQUENCE: 7

Xaa Xaa Xaa Arg
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 8

Arg Ser Arg Lys
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-acyl-Gly

<400> SEQUENCE: 9

Gly Gln Pro Arg
1
```

```
<210> SEQ ID NO 10
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-palmitoyl-Gly

<400> SEQUENCE: 10

Gly Gln Pro Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Palmitoyl-Gly

<400> SEQUENCE: 11

Gly Gln Pro Arg
1

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 12

Lys Thr Thr Lys Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 13

Arg Asp Lys Thr Val
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Palmitoyl-Lys

<400> SEQUENCE: 14

Lys Thr Thr Leu Ser
1               5
```